(12) United States Patent
Hughes et al.

(10) Patent No.: US 7,575,912 B2
(45) Date of Patent: Aug. 18, 2009

(54) **STRAIN OF *RHODOCOCCUS RHODOCHROUS* NCIMB 41164 AND ITS USE AS PRODUCER OF NITRILE HYDRATASE**

(75) Inventors: Jonathan Hughes, Huddersfield (GB); Yvonne Armitage, Holmfirth (GB); Jatinder Kullar, Bradford (GB); Stuart Greenhalgh, Smithfield, VA (US)

(73) Assignee: Ciba Specialty Chemicals Water Treatments Ltd., Bradford (GB)

( * ) Notice: Subject to any disclaimer, the term of this patent is extended or adjusted under 35 U.S.C. 154(b) by 239 days.

(21) Appl. No.: 10/580,448

(22) PCT Filed: Nov. 22, 2004

(86) PCT No.: PCT/EP2004/013252

§ 371 (c)(1), (2), (4) Date: May 23, 2006

(87) PCT Pub. No.: WO2005/054456

PCT Pub. Date: Jun. 16, 2005

(65) Prior Publication Data

US 2007/0077634 A1   Apr. 5, 2007

(30) Foreign Application Priority Data

Dec. 2, 2003 (GB) ................................. 0327907.2
Oct. 6, 2004 (GB) ................................. 0422070.3

(51) Int. Cl.
C12N 1/20 (2006.01)
C12N 1/00 (2006.01)

(52) U.S. Cl. ..................................... 435/252.1; 435/822

(58) Field of Classification Search ....................... None
See application file for complete search history.

(56) References Cited

U.S. PATENT DOCUMENTS

| | | | |
|---|---|---|---|
| 3,281,247 A | 10/1966 | Mieschler | 99/9 |
| 4,931,391 A | 6/1990 | Enomoto et al. | 435/188 |
| 5,089,411 A | 2/1992 | Yamada et al. | 435/244 |
| 5,135,858 A | 8/1992 | Yamada et al. | 435/106 |
| 5,567,608 A | 10/1996 | Doi et al. | 435/182 |
| 5,705,382 A | 1/1998 | Endo et al. | 435/260 |
| 5,827,699 A | 10/1998 | Yanenko et al. | 435/129 |
| 6,146,861 A | 11/2000 | Armitage et al. | 435/128 |
| 6,368,804 B1 | 4/2002 | Ben-Bassat et al. | 435/6 |
| 2004/0048348 A1 | 3/2004 | Murao et al. | 435/170 |
| 2004/0175809 A1 | 9/2004 | Peterson et al. | 435/128 |
| 2004/0175810 A1 | 9/2004 | Peterson et al. | 435/128 |

FOREIGN PATENT DOCUMENTS

| | | |
|---|---|---|
| EP | 0 243 967 | 11/1987 |
| EP | 0 307 926 | 3/1989 |
| EP | 0 362 829 | 4/1990 |
| EP | 0 445 646 | 9/1991 |
| EP | 444 640 | 9/1991 |
| EP | 0 707 061 | 4/1996 |
| RU | 1731814 | 5/1992 |
| RU | 2 077 588 | 4/1997 |
| WO | 02/50297 | 6/2002 |
| WO | 02/088371 | 11/2002 |
| WO | 02/088373 | 11/2002 |

OTHER PUBLICATIONS

Precigou et al; Fems Microbiology Letters, Amsterdam, NL; vol. 204, No. 1, (2001) pp. 155-161.
Watanabe et al.; Japan Soc. For Bioscience, Biotechnology and Agrochem. vol. 51, No. 12, (1987), pp. 3193-3199.
Kobayashi et al.; Biochimica et Biophysica Acta. Gene Structure and Expression, Elsevier, Amsterdam, NL, vol. 1129, No. 1, Dec. 1991.
Ikehata et al., European Journal of Biochemistry, vol. 181, No. 3, (1989), pp. 563-570.
Ingvorsen et al., Ciba Foundation Symposium, vol. 140, 1988, pp. 16-31.
English Language abstract No. 1997-488203[45] of RU 2 077 588.
H. Yamada et al.; Agric. Biol. Chem. vol. 50 (11) pp. 2859-2865 (1986).
T. Nagasawa et al.; Appl. Microbiol Biotechnol vol. 34: pp. 783-788 (1991).
T. Nagasawa et al.; Pure & Appl. Chem. vol. 67, No. 7, pp. 1241-1256 (1995).
T. Leonova et al.; Applied Biochemistry and Biotechnology, vol. 88, (2000), pp. 231-241.
A. Yanenko et al., Proceedings of the Ninth Symposium on the Actinomycetes, (1995), pp. 139-144.
Y. Asano et al.; Agric. Biol. Chem. vol. 46,(5), pp. 1183-1189 (1982).
A. Arnaud et al.; Agric. Biol. Chem. vol. 41, (11), pp. 2183-2191 (1977).
H. Yamada et al.; Biosci. Biotech. Biochem. vol. 60 (9), pp. 1391-1400 (1996).
Nagasawa et al.; Applied Microbilogy and Biotechnology vol. 40, pp. 189-195 (1993).
Chaplin and Bucke; Enzyme Technology (1990)p. 47 published by Cambridge University Press.

*Primary Examiner*—Vera Afremova
(74) *Attorney, Agent, or Firm*—Shiela A. Loggins

(57) ABSTRACT

A microorganism which is *Rhodococcus rhodochrous* strain NCIMB 41164 or a mutant thereof. A method of culturing the microorganism in a culture medium comprising urea or urea derivative is claimed. A nitrite hydratase obtainable from the microorganism is claimed. Also claimed is a process of preparing an amide from the corresponding nitrite wherein the nitrite is subjected to a hydration reaction in an aqueous medium in the presence of a biocatalyst selected from the group consisting of a microorganism which is a *Rhodococcus rhodochrous* strain NUMB 41164, a mutant thereof and a nitrite hydratase obtainable from *Rhodococcus rhodochrous* strain NCIMB 41164 or a mutant thereof. Also claimed is a method of storing the *Rhodococcus rhodochrous* NUMB 41164.

11 Claims, No Drawings

STRAIN OF *RHODOCOCCUS RHODOCHROUS* NCIMB 41164 AND ITS USE AS PRODUCER OF NITRILE HYDRATASE

FIELD OF THE INVENTION

The present invention relates to a microorganism and to methods of culturing and storing the microorganism. The invention also relates to a novel nitrile hydratase enzyme and also to a method of converting a nitrile to an amide employing the nitrile hydratase enzyme.

BACKGROUND

It is well known to employ biocatalysts, such as microorganisms that contain enzymes, for conducting chemical reactions. Nitrile hydratase enzymes are known to catalyse the hydration of nitriles directly to the corresponding amides. Typically nitrile hydratase enzymes can be produced by a variety of microorganisms, for instance microorganisms of the genus *Bacillus, Bacteridium, Micrococcus, Brevibacterium, Corynebacterium, Pseudomonas, Acinetobacter, Xanthobacter, Streptomyces, Rhizobium, Klebsiella, Enterobacter, Erwinia, Aeromonas, Citrobacter, Achromobacter, Agrobacterium, Pseudonocardia* and *Rhodococcus*.

Many references have described the synthesis of nitrile hydratase within microorganisms. Arnaud et al., Agric. Biol. Chem. 41: (11) 2183-2191 (1977) describes the characteristics of an enzyme they refer to as 'acetonitrilase' in *Brevibacterium* sp R312 which degrades acetonitrile to acetate via the amide intermediate. Asano et al., Agric. Biol. Chem. 46: (5) 1183-1189 (1982) isolated *Pseudomonas chlororaphis* B23 which produced nitrile hydratase to catalyse the conversion of acrylonitrile to acrylamide, generating 400 g/L acrylamide. The article by Yamada et al., Agric. Biol. Chem. 50: (11) 2859-2865 (1986) entitled, "Optimum culture conditions for production by *Pseudomonas chlororaphis* B23 of nitrile hydratase", considered the optimisation of the medium components of the growth medium, including the inducer added for nitrile hydratase synthesis. Methacrylamide was found to be the best inducer for this organism. Methacrylamide was included in the culture at the start of growth.

Various strains of the *Rhodococcus rhodochrous* species have been found to very effectively produce nitrile hydratase enzyme.

EP-0 307 926 describes the culturing of *Rhodococcus rhodochrous*, specifically strain J1 in a culture medium that contains cobalt ions. A process is described for biologically producing an amide in which a nitrile is hydrated by the action of a nitrile hydratase produced by *Rhodococcus rhodochrous* J1, which has been cultured in the presence of cobalt ion. The use of various inducers (including crotonamide) is described for the synthesis of nitrile hydratase. In one embodiment an amide is produced in a culture medium of the microorganism in which a substrate nitrile is present. In another embodiment a substrate nitrile is added to the culture medium in which a nitrile hydratase has been accumulated to conduct the hydration reaction. There is also a description of isolating the microbial cells and supporting them in a suitable carrier, for instance by immobilisation, and then contacting them with a substrate. The nitrile hydratase can be used to hydrate nitriles into amides, and in particular the conversion of 3-cyanopyridine to nicotinamide.

EP-0 362 829 describes a method for cultivating bacteria of the species *Rhodococcus rhodochrous* comprising at least one of urea and cobalt ion for preparing the cells of *Rhodococcus rhodochrous* having nitrile hydratase activity. Specifically described is the induction of nitrile hydratase in *Rhodococcus rhodochrous* J1 using urea or urea derivatives which markedly increases the nitrile hydratase activity. Urea or its derivatives are added to the culture medium in one batch at a time or sequentially and cultivation occurs over 30 hours or longer, for instance up to 120 hours.

An article by Nagasawa et al., Appl. Microbiol. Biotechnol. 34: 783-788 (1991), entitled "Optimum culture conditions for the production of cobalt-containing nitrile hydratase by *Rhodococcus rhodochrous* J1", describes isolating J1 as an acetonitrile utilising strain which synthesises two different nitrile hydratases and a nitrilase depending upon the culture conditions used. One nitrile hydratase is induced optimally by urea and urea analogues. Urea is added at the start of the culturing process and seems to become efficient as an inducer only when the basal medium is nutrient rich. Induction of the enzyme started gradually and increased in growth until it reached a maximum after 5 days of cultivation. The activity was found to decrease on prolonged cultivation.

*Rhodococcus rhodochrous* J1, is also used commercially to manufacture acrylamide monomer from acrylonitrile and this process has been described by Nagasawa and Yamada Pure Appl. Chem. 67: 1241-1256 (1995).

Leonova et al., Appl. Biochem. Biotechnol. 88: 231-241 (2000) entitled, "Nitrile Hydratase of *Rhodococcus*", describes the growth and synthesis of nitrile hydratase in *Rhodococcus rhodochrous* M8. The nitrile hydratase synthesis of this strain is induced by urea in the medium, the urea also acting as a nitrogen source for growth by this organism. Cobalt is also required for high nitrile hydratase activity. This literature paper looks at induction and metabolic effects in the main.

Leonova et al., Appl. Biochem. Biotechnol. 88: 231-241 (2000) also states that acrylamide is produced commercially in Russia using *Rhodococcus rhodochrous* M8. Russian patent 1731814 describes *Rhodococcus rhodochrous* strain M8.

*Rhodococcus rhodochrous* strain M33 that produces nitrile hydratase without the need of an inducer such as urea is described in U.S. Pat. No. 5,827,699. This strain of microorganism is a derivative of *Rhodococcus rhodochrous* M8.

The production of acrylamide monomer in particular is desirable via the biocatalytic route. In the review publication by Yamada and Kobayashi, Biosci. Biotech. Biochem. 60: (9) 1391-1400 (1996) titled "Nitrile Hydratase and its Application to Industrial Production of Acrylamide" a detailed account of the development of a biocatalytic route to acrylamide is described. Three successively better catalysts and their characteristics for acrylamide production and in particular the third generation catalyst *Rhodococcus rhodochrous* J1 are described in some detail.

A major disadvantage with the use of biocatalysts is the general lack of stability observed with wet microbial material during storage, transportation and use. Even with relatively stable enzymes and bacteria such as nitrile hydratases in *Rhodococcal* cells, the potential for spoilage before use has led to acceptance within the industry for the need to process the biocatalyst cell suspension in some way e.g. by freezing or freeze-drying of the aqueous mixture or alternatively immobilisation of the cells in some polymer matrix. In order to achieve maximum productivity from the biocatalyst it is important that the maximum biocatalytic activity is retained during its preparation and storage prior to use. In Chaplin and Bucke (1990) In: Enzyme Technology, published by Cambridge University Press, p 47 (Enzyme preparation and use) it was recognised that enzyme inactivation can be caused by heat, proteolysis, sub optimal pH, oxidation denaturants and irreversible inhibitors. A number of substances may cause a reduction in the rate of an enzymes ability to catalyse a reaction. This includes substances that are non-specific protein denaturants, such as urea.

In the presentation, Protein Stability, by Willem J H van Berkel, Wageningen University, factors that may cause deactivation or unfolding were considered and these included proteases, oxidation due to the presence of oxygen or oxygen radicals and denaturing agents causing reversible unfolding, such as urea.

Chaplin and Bucke (1990) In Enzyme Technology, published by Cambridge University Press, p 73 (Enzyme preparation and use) revealed that the key factor regarding the preservation of enzyme activity involves maintaining the conformation of the enzyme structure. Therefore it was considering important to prevent unfolding, aggregation and changes in the covalent structure. Three approaches for achieving this were considered: (1) use of additives; (2) the controlled use of covalent modification; and (3) enzyme immobilisation.

EP-B-0 243 967 describes the preservation of nitrile hydration activity of nitrilase by the addition of stabilizing compounds selected from nitriles, amides and organic acids and their salts, to a solution or suspension of the enzyme or the immobilized form of the enzyme. It clearly states in the description that while a solution or suspension of a microorganism capable of producing nitrilase that hydrates nitriles such as acrylonitrile, to produce the corresponding amides such as acrylamide may be stored at room temperature as long as the storage period is short, storage at a low temperature, especially at a temperature in the vicinity of 0° C. is preferred. It was described in EP-A-0 707 061 that addition of inorganic salts at a concentration of between 100 mM to the saturation concentration of the inorganic salts to an aqueous medium containing either a suspension of microbial cells or immobilized microbial cells, preserved the cells and enzyme activity for a prolonged period of time. This technique is described for the preservation of microbial cells that have nitrile hydratase or nitrilase activity. The addition of bicarbonate or carbonate salts to an aqueous solution of immobilized or unimmobilised microbial cells having nitrilase activity is described in U.S. Pat. No. 6,368,804. Immobilisation has frequently involved removal of the enzyme from the whole cell, before immobilising the enzyme in a matrix. However, although such immobilisation provides very good protection for the enzyme, extraction of the enzyme from the whole cell is an intricate step, which can be time-consuming, expensive and can lead to loss of enzyme. Additionally whole microbial cells can be immobilized. U.S. Pat. No. 5,567,608 provides a process of immobilising whole cell biocatalyst in a cationic copolymer which has good storage stability and prevents putrefaction.

*Rhodococcus rhodochrous* J1, which is used commercially to manufacture acrylamide monomer, is immobilised to (a) allow transportation and (b) to increase the longevity of the biocatalyst in use. In U.S. Pat. No. 5,567,608 the inventors state that biocatalysts are normally immobilized for use on an industrial scale, to facilitate ease of separation of the biocatalyst from the reaction product, preventing impurities from the biocatalyst eluting into the product and to assist in continuous processes and recycling of the biocatalyst. However, immobilisation is an extra processing step that requires an additional plant and the use of potentially a number of other raw materials such as alginate, carrageenan, acrylamide and other acrylate monomers, and vinyl alcohol. Thus, this is an expensive processing step.

Various other ways have been proposed for minimising the deleterious effects of enzyme inactivation in an attempt reduce the negative impact on a chemical reaction process.

It is also known to freeze dry biocatalysts in order to preserve the activity of an enzyme in storage over a prolonged period of time. Again this is a potentially expensive processing step that is normally carried out with biocatalysts prepared on a small scale. Cryopreservation in liquid nitrogen or in the vapour phase of liquid nitrogen also affords long-term storage of microbial cells but requires a constant supply of liquid nitrogen. Freezing of recovered biomass or semi-pure or pure enzymes at temperatures of <−18° C. is also known to preserve biocatalytic activity for prolonged periods of time.

Furthermore, once the cell mass is introduced to the reactor and the reaction is taking place minimisation of the loss of efficacy is critical to the operational efficiency and the process economics. Once again, immobilisation of the microbial cells into some polymer matrix is standard procedure to optimise these process parameters.

It would therefore be desirable to provide a process and a biocatalyst where these disadvantages can be overcome.

SUMMARY OF THE INVENTION

According to the present invention we provide a microorganism that is *Rhodococcus rhodochrous* strain NCIMB 41164 or a mutant thereof.

This new microorganism has been found to readily produce nitrile hydratase. We have found that this new microorganism (and the nitrile hydratase produced therefrom) can be used in a process of converting nitriles, to the amide. *Rhodococcus rhodochrous* NCIMB 41164 is particularly of use for the conversion of (meth)acrylonitrile to (meth)acrylamide. The microorganism and enzyme have been found to remain active, and in some cases even increase in activity, over long periods of time and furthermore can be recovered from the reaction mixture with undiminished activity after preparation of acrylamide at >50% w/w. Thus it can be, if required, reused either directly or after a further period of storage.

The details of the new strain *Rhodococcus rhodochrous* NCIMB 41164 are given below:

1. Origin and Deposition

The *Rhodococcus rhodochrous* strain was isolated by us from soil in Bradford, England and deposited on Mar. 5, 2003 at the National Collection of Industrial and Marine Bacteria (NCIMB), where it was assigned the accession number NCIMB 41164 under the Budapest Treaty.

NCIMB Ltd.

Ferguson Building

Crabstone Estate

Bucksburn, Aberdeen

Scotland, AB219YA

2. Taxonomic Identification of the Microorganism

Identification of the soil isolate was carried out using the technique of 16S rDNA analysis. The sequence of the 16S rDNA gene obtained from the soil isolate was compared with nucleic acid sequence databases. The sequence obtained was compared to those found in a proprietary database (Microseq™) and the top 20 hits were determined. Comparison of the sequence with this database identified the best match as *Rhodococcus rhodochrous* with a 97.48% similarity. This is a genus level match, but was most likely to be a strain of *Rhodococcus rhodochrous*. A further search search against the public EMBL database identified the best match for this database to *Rhodococcus rhodochrous* with 99.698% similarity.

3. Morphological and Cultural Characteristics
   (1) Polymorphic growth
   (2) Motility: immotile
   (3) Non-spore former
   (4) Gram positive
   (5) Aerobic
   (6) Growth on nutrient agar gives salmon pink round colonies within 48 hours at 30° C.

4. Cultivation and Nitrile Hydratase Synthesis

The *Rhodococcus rhodochrous* NCIMB 41164 of the present invention can be cultured under any conditions suitable for the purpose in accordance with any of the known methods, for instance as described in the aforementioned prior art. Preferably the microorganism is cultured in a culture medium that comprises urea or a derivative of urea. We have found that this microorganism can be grown in a medium containing acetonitrile or acrylonitrile as an inducer of the nitrile hydratase. In the presence of urea or urea derivative as an inducer and cobalt chloride as a source of cobalt ions, very high nitrile hydratase activity is achieved. For example urea and cobalt are added to the medium described in the experimental examples.

Desirably the *Rhodococcus rhodochrous* NCIMB 41164 can be cultured to give high enzyme activity, for instance about 250-300,000 µmol min$^{-1}$/g dry biomass at 15° C. High nitrile hydratase activity can be achieved if urea or a urea derivative is present in the culture medium. It may be present at the start of the culture or it may be added at some point during growth, but generally should be added before the onset of the stationary phase of growth. High nitrile hydratase activity can preferably be achieved if urea or the urea derivative is not present in any substantial amount in the culture medium at the start of the microorganism growth but is introduced later. By this we mean that urea or the urea derivative is not present or is present in an amount of less than 0.2 g/l, preferably less than 0.1 g/l. More preferably the culture medium is substantially free (i.e less than 0.2 g/l) of urea or the urea derivative for at least the first six hours of microorganism growth. It is especially preferred if the growth medium of the microorganism is substantially free of urea or the urea derivative for at least 12 hours and in some cases at least 24 hours before the introduction of the urea or the urea derivative as the growth rate of the microorganism is higher in the absence of urea or the urea derivative, but that it is added before 48 hours culturing of the microorganism. We have found that this enables higher nitrile hydratase activity to occur in a shorter period of time than if the urea or the urea derivative had been added at the start of culturing.

The invention also relates to a nitrile hydratase obtainable from a microorganism which is *Rhodococcus rhodochrous* NCIMB 41164 or a mutant thereof.

DETAILED DESCRIPTION OF THE INVENTION

A further aspect of the invention concerns a process of preparing an amide from the corresponding nitrile wherein the nitrile is subjected to a hydration reaction in an aqueous medium in the presence of a biocatalyst selected from the group consisting of a microorganism which is *Rhodococcus rhodochrous* NCIMB 41164, a mutant thereof and a nitrile hydratase obtainable from *Rhodococcus rhodochrous* NCIMB 41164 or a mutant thereof. Hereafter the term 'biocatalyst' refers to the nitrile hydratase that is synthesised within the *Rhodococcus rhodochrous* NCIMB 41164 cell and may include the *Rhodococcus rhodochrous* NCIMB 41164 cell itself. Thus, the biocatalyst could be used as a whole cell preparation in a fermentation medium, as an aqueous suspension, as a recovered cell paste as an immobilized cell preparation or as any other form of the nitrile hydratase suitable for the conversion of nitrile to amide that satisfies the requirements of this invention.

This process is particularly suitable for readily preparing an amide from the corresponding nitrile. In particular aqueous solutions of amide can be prepared in high concentration. The process is especially suitable for preparing acrylamide or methacrylamide.

The biocatalyst may be used as a whole cell catalyst for the generation of amide from nitrile. It may be immobilised for instance entrapped in a gel or it may be used preferably as a free cell suspension. Alternatively the nitrile hydratase enzyme may be extracted and for instance used directly in the process of preparing the amide.

In one preferred way of carrying out the process the biocatalyst is introduced into an aqueous medium suitable for carrying out the culturing of the microorganism. Typically a suspension of the biocatalyst, for instance whole cells of the microorganism, may be formed. A nitrile, for instance acrylonitrile or methacrylonitrile is fed into the aqueous medium comprising the biocatalyst in such a way that the concentration of (meth) acrylonitrile in the aqueous medium is maintained at up to 6% by weight. Nitrile such as acrylonitrile or methacrylonitrile is more preferably fed into the reaction medium and the reaction allowed to continue until the concentration of amide, for instance acrylamide or methacrylamide reaches the desired level, in particular between 30 and 55% by weight. Most preferably the concentration is around 50% by weight.

This new strain of *Rhodococcus rhodochrous* (NCIMB 41164) is capable of producing aqueous acrylamide solutions in high concentration (for instance 50% acrylamide). Desirably the reaction may be carried out as a free cell process using a fed-batch type reactor to which the biocatalyst (*Rhodococcus rhodochrous* NCIMB 41164) is added in the form of fermentation broth or as harvested biomass.

The activity of the biocatalyst (*Rhodococcus rhodochrous* NCIMB 41164) and the nitrile hydratase produced therefrom is such that it can be recycled and reused for further hydration of nitrile to the corresponding amide.

Recycling of the biocatalyst is particularly suitable for any case of converting (meth) acrylonitrile to (meth) acrylamide. Thus in the manufacture of acrylamide when the reaction process is complete and acrylamide has been produced at the appropriate concentration, the catalyst can be removed and re-used to produce another batch of acrylamide without loss in nitrile hydratase activity. This can even be achieved after the biocatalyst has been stored in water for several days (for instance three days) prior to reuse. It is even possible to prepare a third batch of acrylamide, even after further storage.

According to one aspect of the invention we provide an aqueous composition comprising a biocatalyst that is or is obtainable from the microorganism *Rhodococcus rhodochrous* strain NCIMB 41164 or a mutant thereof and wherein the biocatalyst is in the form of a non-actively growing free cell microorganism. We also provide a method of storing the biocatalyst, that is in the form of a non-actively growing free cell microorganism.

The microbial cells of the biocatalyst used to carry out the conversion of nitrile to amide, may be regarded as a non-actively growing culture. By this we mean that the medium and the storage conditions in which the microorganism is held would not be expected to promote growth. The storage medium can for instance be the *Rhodococcus rhodochrous* NCIMB 41164 cells that may be recovered from the fermentation medium. Or the cells may be used directly in the fermentation medium, or they may be present as an aqueous suspension in a suitable suspending medium for instance; water; physiological saline solution; a suitable buffer solution such as phosphate buffer or any other similar buffer or a growth medium where metabolism in the microorganism cells is substantially zero as determined by measuring the growth rate, or the biomass concentration or oxygen consumption or nutrient consumption, or other form of measurement generally used to monitor microbial growth and metabolism.

The composition or the storage medium may comprise any residual fermentation broth components. The fermentation broth may include any of the typical ingredients used for culturing the microorganism and also may include products and by-products produced by the microorganism. Typical components of the fermentation broth include sugars, polysaccharides, proteins, peptides, amino acids, nitrogen sources, inorganic salts, vitamins, growth regulators and enzyme inducers. Specifically this could include monosaccharides or disaccharides as sugars; ammonium salts or other nitrogen sources; inorganic salts such as phosphates, sulphates, magnesium, calcium, sodium and potassium salts; metal compounds; vitamins; and complex fermentation medium components, for example corn steep liquor; peptone; yeast extract; organic or inorganic compounds that may be used for specific microbial growth requirements; specific enzyme inducers (such as urea that is used to induce the nitrile hydratase of *Rhodococcus rhodochrous* NCIMB 41164); and organic acids such as citrate or pyruvate; and any other organic or inorganic compounds that may be required to ensure successful growth of the *Rhodococcus rhodochrous* NCIMB 41164.

Usually when a biocatalyst, such as one that produces nitrile hydratase, is stored without continued growth for a period of time, even for a few days, it is normal to remove the microbial cells from the fermentation broth, whether it is the cells that are required as the catalyst, or whether the enzyme is recovered from the cells or fermentation medium. This is to prevent microbial growth in the fermentation broth causing putrefaction of the broth and to reduce protease activity that can cause the breakdown of the enzyme that is required. It is normal therefore to preserve the fermentation broth per se or to remove the cells to prevent the degradation of the biocatalyst through extraneous biological activity such as microbial contamination. The biocatalytic activity could normally be expected to reduce in a very short period of time such as within a day and certainly in less than two days if this were not carried out.

Methods of preserving the activity during the storage of biocatalysts, even for periods of time up to one-week, have normally involved removal of the biocatalyst from the fermentation broth and/or immobilisation of the biocatalyst in a suitable matrix and/or stabilisation using stabilising substances which then either become contaminants in the reaction mixture and this may be a problem further downstream or an additional processing step is required to remove the stabilizing compound or additive from the microbial cell suspension before it is used as a biocatalyst.

In the absence of such preservation treatments and normally biocatalysts that are kept at ambient temperatures tend to lose activity to the extent that they are no longer as effective or even suitable for catalysing reactions.

Growth of a microorganism for use as a biocatalyst may take place over a period of several days. During this time the microorganism is actively growing, that is to say balanced growth where the biomass is increasing together with an increase in and maintenance of the overall chemical composition of the cell.

Normally the growth of microorganisms is limited either by the exhaustion of nutrient or the accumulation of toxic products of metabolism and the growth rate reduces. Growth is maintained by feeding appropriate nutrients and maintaining a correct temperature and pH for growth and where required supplying oxygen.

The storage method described here promotes effective stability such that the biocatalyst can be readily used without any significant loss in activity. Storage stability is achieved without the necessity of resorting to for instance immobilisation, addition of stabilizing compounds or freeze drying. Storage stability may be achieved without resorting to removal of any of the fermentation broth components such as urea or urea derivatives, even though urea is a known protein deactivator.

The composition or the environment used in the method of storage may contain oxygen or can be a substantially oxygen free environment. By oxygen free we mean that the concentration of oxygen should be less than 1% dissolved oxygen concentration Removal of oxygen from the fermentation broth can be achieved by any of the conventional methods for removing oxygen. These include purging for a period of time with an inert gas, removal of any head-space in the storage container, storing under diminished pressure or the addition of known oxygen scavengers such as ascorbic acid or hydrazine and hydrazide.

It would have been expected that after 2 days and especially after several days storage there would be some loss in nitrile hydratase activity. This would have been expected even in the absence of oxygen. It would have been expected especially in the presence of residual fermentation broth components, such as urea, and also at temperatures of above 0° C. This is because protease enzymes in the biocatalyst might be expected to break down other proteins in the cell, including the nitrile hydratase. Furthermore, the presence of urea or urea derivative could be expected to be detrimental, since urea is known to be a protein deactivator. However, the biocatalyst suffers none of the expected disadvantages and thus suffers no significant loss in nitrile hydratase activity.

On the contrary we find that during the storage period the activity of the biocatalyst comprising nitrile hydratase can in some cases actually increase. Thus in another aspect of the invention we provide a method of increasing the nitrile hydratase activity of a biocatalyst capable of forming nitrile hydratase by storing the biocatalyst in a storage medium in accordance with the storage method of the present invention. Therefore, the method can result in a new biocatalyst composition by virtue of its increased activity. Therefore, nitrile hydratase of the biocatalyst composition, and in particular formed during storage of the biocatalyst, is new. Also, the biocatalyst does not produce the mal odours associated with putrefaction during the storage period.

Preferably the storage method allows the biocatalyst to be stored for at least two days and more preferably one or more weeks. In particular the biocatalyst may be stored from three to twenty eight days, for example 3 to 14 days.

The presence of fermentation broth components such as urea are not essential to the composition or the storage method of this aspect of invention. Where fermentation broth components are present, this may be urea or a urea derivative. The urea derivative can be for example an alkyl derivative of urea.

Urea or the urea derivative could be present in the biocatalyst composition through its inclusion in the fermentation mixture. In one form of the invention the composition or storage medium containing the biocatalyst may be deoxygenated and contain fermentation broth components such as urea.

A particularly advantageous feature of this aspect of the invention is that it is no longer necessary to separate the biocatalyst from the fermentation mixture in which it was cultured. This is of significant value since it avoids the requirement for an additional processing step. Therefore the composition may also comprise a fermentation mixture, which is then stored. In the method of storing the biocatalyst, we find that this may also be achieved in the presence of a fermentation mixture without any detrimental effects on the activity of the enzyme. This then allows the fermentation broth to be used immediately to catalyse the reaction, or to allow it to be stored for several days or even weeks without detriment whilst the bioconversion step is being carried out also over a period of several days, thus ensuring a constant supply of readily available biocatalyst without need for additional processing steps thus simplifying and reducing the cost of the bioconversion step.

The biocatalyst may conveniently be stored at temperatures above its freezing point. Typically the biocatalyst may be stored at ambient temperatures, for instance up to 30 or 40° C. However, the advantage of the present method is that the biocatalyst may be stored at ambient temperatures without any special precautions for monitoring and controlling the temperature. Preferably the biocatalyst is stored at a temperature between 4 and 30 or 40° C., more preferably between 5 and 25° C., such as between 10 and 25° C. and in particular 15 to 25° C.

According to a further aspect of the present invention we provide a method of producing an amide by contacting the corresponding nitrile by a nitrile hydratase, in which the biocatalyst is part of a composition or stored in the form of a non-actively growing free cell microorganism in a storage medium in which the composition or storage medium comprises fermentation broth, and the biocatalyst is (or is obtainable from) the microorganism *Rhodococcus rhodochrous* strain NCIMB 41164 or a mutant thereof.

Thus in accordance with this aspect of the invention the biocatalyst may have been held in an environment containing oxygen or held in an oxygen-free environment. It may or may not contain residual fermentation broth components such as urea prior to commencing the conversion of the nitrile. This may be resulting from storing the biocatalyst in accordance with the storage aspect of the present invention or alternatively provided as a composition in accordance with the present invention.

As given previously it is not necessary to remove the biocatalyst from the fermentation mixture in which the biocatalyst has been prepared. Thus in a preferred form the environment in which the biocatalyst is held also contains components of a fermentation broth. Therefore a biocatalyst composition containing components of a fermentation broth can be combined with a nitrile which is then hydrated to the corresponding amide. We have found surprisingly that in contrast to previous knowledge, for instance in U.S. Pat. No. 5,567,608 states that immobilisation of the biocatalyst is preferable to prevent elution of impurities from the biocatalyst into the reaction product, that the inclusion of fermentation broth in the reaction mixture does not affect the quality of the final product and this aspect is described in our co-filed UK application 0327901.5, identified by case number BT/3-22349/P1.

The fermentation mixture will comprise essential components for allowing microorganisms to be grown and sustained. In general the mixture will at least contain a carbon source, nitrogen source and various nutrients. This may include a saccharide for instance a monosaccharide such as glucose or other sugar or a disaccharide or polysaccharide, ammonium salts, complex medium components such as yeast extract and peptone, amino acids, vitamins, phosphate salts, potassium, sodium, magnesium and calcium salts, trace elements such as iron, cobalt, manganese, copper, zinc and the like. These and other ingredients can be included in the fermentation mixture at concentrations suitable for the particular microorganism. It is known that fermentations can be subject to changes in the productivity of the biocatalyst and the fermentation broth may be used at different stages of growth and so it is important to be able to store the biocatalyst after production in such a way.

We find that the activity of the biocatalyst does not diminish significantly during the reaction for a prolonged period. Consequently the biocatalyst may be replaced less frequently. Preferably the biocatalyst is used for a period of at least 2 days and loses substantially no activity over that period.

Generally the catalysis of the reaction using nitrile hydratase enables the nitrile to be converted into the corresponding amide in a single step. This process is of particular value when the nitrile is acrylonitrile and the amide is acrylamide. It is desirable to carry out this conversion step several times using a single batch of biocatalyst from which portions are removed over a period of several days to carry out several reactions where nitrile is converted to amide. Thus, it is important to be able to store the biocatalyst as inexpensively as possible without detriment to the catalyst whilst the bioconversion step is carried out simultaneously. So in effect one batch of biocatalyst can be stored ready for use to make several batches of for instance acrylamide. Several batches could be from 5 to 10 or more batches, even 15 to 20 batches.

In a further aspect of the invention we have found a way of improving the biocatalytic activity of a microorganism. The microorganism would be cultured in a culture medium that comprises urea or a derivative of urea. However, urea or the derivative of urea is introduced into the culture medium at least six hours after the start of growth of the microorganism. Normally the culture medium is substantially free of urea or the urea derivative for at least the first six hours of culturing the microorganism and thereafter urea or a urea derivative is added to the culture medium. As indicated previously by substantially free we mean that the culture medium contain less than 0.2 g/l, usually less than 0.1 g/l and may contain no urea or the urea derivative. Preferably the culture medium is substantially free of urea or the urea derivative for at least 12 hours and sometimes at least 24 hours. However, in order to maximise the biocatalytic activity it is preferred to introduce the urea or the urea derivative within 48 hours of culturing.

The biocatalytic activity can be established in terms of enzyme activity as described herein.

Preferably the microorganism is capable of producing a nitrile hydratase. Suitably a biocatalyst comprising such a microorganism can be used to prepare amides from the corresponding nitrile by a hydration process in which nitrile hydratase catalyses the reaction. The culturing of the microorganism by delayed introduction of urea or urea derivative provides increased nitrile hydratase activity particularly suitable for this reaction. The process is particularly suitable for the preparation of (meth) acrylamide from (meth) acrylonitrile. Such a process may be carried out as described herein. In addition the biocatalyst may be recycled and reused.

It is particularly desirable that the microorganism is of the *Rhodococcus* genus, preferably a *Rhodococcus rhodochrous* species, especially *Rhodococcus rhodochrous* NCIMB 41164.

The following examples provide an illustration of how to carry out the invention.

Example 1

*Rhodococcus rhodochrous* NCIMB 41164 was isolated from soil using an enrichment culture technique and it was grown on a medium containing the following constituents (g/l): $KH_2PO_4$, 7.0; $KH_2PO_4$, 3.0; peptone, 5.0; yeast extract, 3.0; glucose, 5.0; $MgSO_4$, 0.5; trace metals solution, 5 ml; acetonitrile, 20 ml. The pH was adjusted to 7.2. The nitrile hydratase activity was 4,000 μmol $min^{-1}$/g dry cells at 15° C. after 3 days growth at 28° C.

Example 2

(1) *Rhodococcus rhodochrous* NCIMB 41164 was grown in a 2 L baffled Erlenmeyer flask containing 400 mL culture medium containing the following constituents (g/L): dipotassium hydrogen phosphate 0.7; Potassium hydrogen phosphate 0.3; glucose 10.0; peptone, 1.0; yeast extract 3.0; magnesium sulphate heptahydrate 0.5; Urea 5.0; cobalt chloride hexahydrate 0.01; tap water to 1 L. The pH of the medium was adjusted to pH 7.2. The culture was grown at 28° C. for 5 days after which the nitrile hydratase activity was 47,900 μmol $min^{-1}$/g at 15° C.

(2) (a) *Rhodococcus rhodochrous* NCIMB 41164 was grown in the medium described in (1) except that peptone was omitted.

(b) *Rhodococcus rhodochrous* NCIMB 41164 was grown in the medium described in (2a) except that peptone was omitted as was urea. The organism was cultured for 24 hours and then 5 g/L urea was added to the culture which was grown for a further 5 days.

(C) *Rhodococcus rhodochrous* NCIMB 41164 was grown in the medium described in (2a) except that urea was not included in the medium. The organism was cultured for 48 hours and then 5 g/L urea was added to the culture which was grown for a further 4 days.

(d) *Rhodococcus rhodochrous* NCIMB 41164 was grown in the medium described in (2a) except that urea was not included in the medium. The organism was cultured for 6 days.

Samples were taken from the four cultures described above at time=1, 2, 3 and 6 days after growth commenced. The nitrile hydratase activities were measured at 15° C., see table 1.

TABLE 1

| Urea addition | Nitrile Hydratase Activity μmol $min^{-1}$/mg dry cells | | | |
|---|---|---|---|---|
| time (days) | T = 1 day | T = 2 days | T = 3 days | T = 6 days |
| 0 | 9.1 | 24.2 | 24.8 | 37.6 |
| 1 | 1.0 | 21.6 | 49.3 | 41.3 |
| 2 | ND | ND | 15.1 | 15.3 |
| None added | 0.94 | ND | 0.46 | 0.98 |

ND not determined

Example 3

(1) *Rhodococcus rhodochrous* NCIMB 41164 was grown in a 280 L fermenter containing 180 L culture medium containing the following constituents (g/L): diPotassium hydrogen phosphate 0.7; Potassium hydrogen phosphate 0.3; glucose 2.0; yeast extract 3.0; magnesium sulphate heptahydrate 0.5; cobalt chloride hexahydrate 0.01. The pH of the medium was adjusted to pH 7.2. The culture was grown at 30° C. for 3 days. Urea was added to the culture after 17 h. The nitrile hydratase activity was measured (at 30° C.) periodically. 22 h after the urea was added the activity was approximately 176,000 μmol $min^{-1}$/g at 30° C. and after a further 9 h the activity had increased to 323,000 μmol $min^{-1}$/g.

(2) 625 g of water was charged to the reactor to which *Rhodococcus rhodochrous* NCIMB 41164 was added. The mixture was heated to 25° C. Acrylonitrile 375 g was fed to the reactor at a rate to maintain the concentration at 2% (w/w). After 175 minutes all of the acrylonitrile had been converted to acrylamide to a final concentration of approximately 50% (w/w).

(3) The cells from 2 were recovered by centrifugation and they were suspended in 625 g water. This suspension was stored at 4° C. for 3 days prior to re-charging to the reactor. The procedure described in 5 was followed and again after 175 minutes all of the acrylonitrile was converted to acrylamide.

(4) The cells from 3 were treated as described in 3 above except they were stored for 2 days prior to re-use. Again 50% acrylamide was synthesised. The acrylic acid concentrations measured for the batches of acrylamide generated in example 32-4)(5-7 are shown in Table 2.

TABLE 2

Acrylic acid concentrations measured in each of the acrylamide batches

| Example number | Acrylic Acid Concentration (ppm) |
|---|---|
| 3-2 | 5650 |
| 3-3 | 102 |
| 3-4 | None detected (<10 ppm) |

Example 4

(1) *Rhodococcus rhodochrous* NCIMB 41164 was grown in a 280 L fermenter containing 180 L culture medium containing the following constituents (g/L): dipotassium hydrogen phosphate 0.7; Potassium hydrogen phosphate 0.3; glucose 1.0; yeast extract 3.0; magnesium sulphate heptahydrate 0.5; cobalt chloride hexahydrate 0.01; urea, 5.0. The pH of the medium was adjusted to pH 7.2. The culture was grown at 30° C. for 3 days.

25 L of the fermentation broth was degassed with nitrogen for 20 minutes prior to storage at ambient temperature, which was approx. 5° C. for 3½ days. The nitrile hydratase activity was measured 15 h after harvesting and it was found to be 242,000 U/g at 25° C. When the NH activity was re-measured 3 days later it was found to be 293,000 U/g.

Example 5

*Rhodococcus rhodochrous* NCIMB 41164 was grown in a 2 L Erlenmeyer flask for 5 days at 28° C. with shaking at 180 rpm in a culture medium containing the following constituents in g/L: dipotassium hydrogen phosphate 0.7; Potassium hydrogen phosphate 0.3; glucose 10.0; yeast extract 3.0; urea 5.0; magnesium sulphate heptahydrate 0.5; cobalt chloride hexahydrate 0.01. The pH of the medium was adjusted to pH 7.2. The culture broth was divided into two portions, one half of which was deoxygenated using nitrogen. Portions of both the deoxygenated and the oxygenated culture broth were incubated at 4, 15 and 25° C. for 1 week. The nitrile hydratase activity of the portions was measured periodically.

The results of the nitrile hydratase assays are shown in Table 3. The results are given in U/mg dry cells

TABLE 3

| Incubation temp. | Time (days) | | | | | |
|---|---|---|---|---|---|---|
| | 0 | 1 | 2 | 3 | 5 | 7 |
| 4° C. (O2) | 140 | 286 | | 232 | 267 | 257 |
| 4° C. (degassed) | | 274 | | | 214 | 293 |
| 15° C. (O2) | | | | | | |
| 15° C. (degassed) | 140 | 218 | | | | |
| 25° C. (O2) | 140 | 143 | | | | |
| 25° C. (degassed) | | 154 | 230 | | | |

It can be seen from the results in Example 5 that the biocatalyst can be stored effectively at ambient temperatures. Furthermore it can be seen that the nitrile hydratase activity increased on this occasion on storage in comparison to day zero.

Example 6

Defrosted cells of *Rhodococcus rhodochrous* NCIMB 41164 were resuspended in water. The nitrile hydratase activity was measured over a period of 1 week. The relative nitrile hydratase activities measured are shown in Table 4.

TABLE 4

| | Relative nitrile hydratase activity (%) | | |
|---|---|---|---|
| Time (days) | 4° C. | 15° C. | 25° C. |
| 0 | 100 | 100 | 100 |
| 1 | 66 | 64 | 66 |
| 2 | 78 | 77 | 76 |
| 5 | 72 | 72 | 74 |
| 7 | 68 | 74 | 73 |

The results in Table 4 show that the activity did not decrease at any of the temperatures of storage between the 1 and 7 day incubation period.

Example 7

(1) *Rhodococcus rhodochrous* NCIMB 41164 was grown in a 0.5 L baffled Erlenmeyer flask containing 100 mL culture medium containing the following constituents (g/L): diPotassium hydrogen phosphate 0.7; Potassium hydrogen phosphate 0.3; glucose 10.0; yeast extract 3.0; magnesium sulphate heptahydrate 0.5; Urea 5.0; cobalt chloride hexahydrate 0.01; tap water to 1 L. The pH of the medium was adjusted to pH 7.2. The culture was grown at 30° C. for 4 days. The nitrile hydratase activity was measured at 25° C. after 2, 3 and 4 days growth.

(2) (a) *Rhodococcus rhodochrous* NCIMB 41164 was grown in the medium described in (1) except that the urea was replaced by dimethylurea.

(b) *Rhodococcus rhodochrous* NCIMB 41164 was grown in the medium described in (1) except that the urea was replaced by ethylurea.

(c) *Rhodococcus rhodochrous* NCIMB 41164 was grown in the medium described in (1) except that 2.5 g/l urea and 2.5 g/l dimethylurea were added to the medium in place of the 5 g/l urea.

(d) *Rhodococcus rhodochrous* NCIMB 41164 was grown in the medium described in (1) except that 2.5 g/l urea and 2.5 g/l ethylurea were added in place of the 5 g/l urea.

The nitrile hydratase activities are shown in Table 5

TABLE 5

| | Nitrile hydratase activity (μmol/min/g dry cells) | | |
|---|---|---|---|
| Urea compound | 2 days | 3 days | 4 days |
| urea | 6,800 | 34,800 | 123,200 |
| Dimethylurea | 14,600 | 73,800 | 97,600 |
| Ethylurea | 14,500 | 110,100 | not determined. |
| Urea + dimethylurea | 7,400 | 27,000 | 19,400 |
| Urea + ethylurea | 6,000 | 6,900 | 73,850 |

The invention claimed is:

1. An isolated microorganism which is *Rhodococcus rhodochrous* strain NCIMB 41164.

2. A method of culturing the microorganism *Rhodococcus rhodochrous* strain NCIMB 41164 in a culture medium that contains urea or a derivative of urea.

3. A method according to claim 2 in which urea or urea derivative is introduced into the culture medium at least six hours after the start of growth of the microorganism.

4. A method according to claim 2 in which the culture medium contains less than 0.2 g/l urea or the urea derivative for at least the first 6 hours of culturing the microorganism and thereafter urea or the urea derivative is added to the culture medium.

5. A method according to claim 2 in which the culture medium contains less than 0.2 g/l urea or the urea derivative for at least the first 12 hours of culturing the microorganism and thereafter urea or the urea derivative is added to the culture medium.

6. A method according to claim 2 in which urea or the urea derivative is added to the culture medium within 48 hours of culturing.

7. A method of improving the biocatalytic activity of a microorganism according to claim 1, in which the microorganism is cultured in a culture medium that comprises urea or a derivative of urea,
  wherein urea or the derivative of urea is introduced into the culture medium at least 6 hours after the start of growth of the microorganism.

8. A method according to claim 7 in which the culture medium contains less than 0.2 g/l urea or the derivative of urea for at least the first 6 hours of culturing the microorganism and thereafter urea or the derivative of urea is added to the culture medium.

9. A method according to claim 7 in which the culture medium contains less than 0.2 g/l urea or the derivative of urea for at least the first 12 hours of culturing the microorganism and thereafter urea or the derivative of urea is added to the culture medium.

10. A method according to claim 7 in which urea or the urea derivative is added to the culture medium within 48 hours of culturing.

11. An aqueous composition comprising a biocatalyst that is the microorganism *Rhodococcus rhodochrous* strain NCIMB 41164 and wherein the biocatalyst is in the form of a non-actively growing free cell microorganism.

* * * * *

UNITED STATES PATENT AND TRADEMARK OFFICE
CERTIFICATE OF CORRECTION

PATENT NO. : 7,575,912 B2 Page 1 of 1
APPLICATION NO. : 10/580448
DATED : August 18, 2009
INVENTOR(S) : Hughes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 316 days.

Signed and Sealed this

Seventh Day of September, 2010

David J. Kappos
*Director of the United States Patent and Trademark Office*